(12) United States Patent
Backes et al.

(10) Patent No.: US 9,169,227 B2
(45) Date of Patent: *Oct. 27, 2015

(54) PRODUCTION OF 5 HYDROXYMETHYULFURFURAL (HMF) FROM HEXOSE SOLUTIONS IN THE PRESENCE OF STEAM

(71) Applicant: BASF SE, Ludwigshafen (DE)

(72) Inventors: René Backes, Lampertheim (DE); Benoit Blank, Mannheim (DE); Alois Kindler, Grünstadt (DE); Carmen Feldner, Ludwigshafen (DE)

(73) Assignee: BASF SE (DE)

( * ) Notice: Subject to any disclaimer, the term of this patent is extended or adjusted under 35 U.S.C. 154(b) by 82 days.

This patent is subject to a terminal disclaimer.

(21) Appl. No.: 13/711,717

(22) Filed: Dec. 12, 2012

(65) Prior Publication Data

US 2013/0150596 A1    Jun. 13, 2013

Related U.S. Application Data

(60) Provisional application No. 61/569,795, filed on Dec. 13, 2011.

(51) Int. Cl.
C07D 307/48 (2006.01)
C07D 307/46 (2006.01)

(52) U.S. Cl.
CPC ............ *C07D 307/48* (2013.01); *C07D 307/46* (2013.01)

(58) Field of Classification Search
None
See application file for complete search history.

(56) References Cited

U.S. PATENT DOCUMENTS

| 2,929,823 A | 3/1960 | Garber et al. |
| 3,201,331 A | 8/1965 | Hunter |
| 4,740,605 A | 4/1988 | Rapp |

FOREIGN PATENT DOCUMENTS

| CN | 102399203 A | 4/2012 |
| DE | 3601281 A1 | 7/1987 |
| EP | 1834950 A1 | 9/2007 |
| EP | 1834951 A1 | 9/2007 |
| FR | 2663933 A1 | 1/1992 |

OTHER PUBLICATIONS

Descores et al. FR 2664273 A1, Jan. 10, 1992, machine translation.*
Glover, Selecting Evaporators for Process Applications, Reprinted from Chemical Engineering Progress, Dec. 2004.*
Lewkowski, ARKIVOC 2001 (i) 17-54.*
Chheda, J. et al., "Production of 5-hydroxymethylfurfural and furfural by dehydration of biomass-derived mono-and poly-saccharides", Green Chem., vol. 9, (2007), p. 342-350.
International Search Report for PCT/EP2012/075055, mailing date Jan. 30, 2013.
Kuster, B., "5-Hydroxymethylfurfural (HMF). A Review Focussing on its manufacture", vol. 42, No. 8, (1990), p. 314-321.
van Dam, H.E., et al., "The Conversion of Fructose and Glucose in Acidic Media: Formation of Hydroxymethylfurfural", Starch/starke, vol. 38, (1986), pp. 95-101.
Rosatella, A., et al., "5-Hydroxymethylfurfural (HMF) as a Building Block Platform: Biological Properties, Synthesis and Synthetic Applications", Green Chem, vol. 13, (2011). pp. 754-793.

* cited by examiner

*Primary Examiner* — Layla Bland
(74) *Attorney, Agent, or Firm* — Drinker Biddle & Reath LLP

(57) ABSTRACT

Method for producing 5-hydroxymethylfurfural (HMF), wherein
a) solutions (hereinbelow called starting solution) which comprise
   a hexose and
   an organic solvent with a boiling point greater than 200° C. (at standard pressure) (for short called high-boiling component),
   and steam are fed to a reaction vessel,
b) in the reaction vessel, a conversion of the hexose to HMF takes place in the presence of steam with the simultaneous distillative removal of the HMF and
c) as distillate, an aqueous, HMF-comprising solution (hereinbelow called distillate) is obtained.

17 Claims, 1 Drawing Sheet

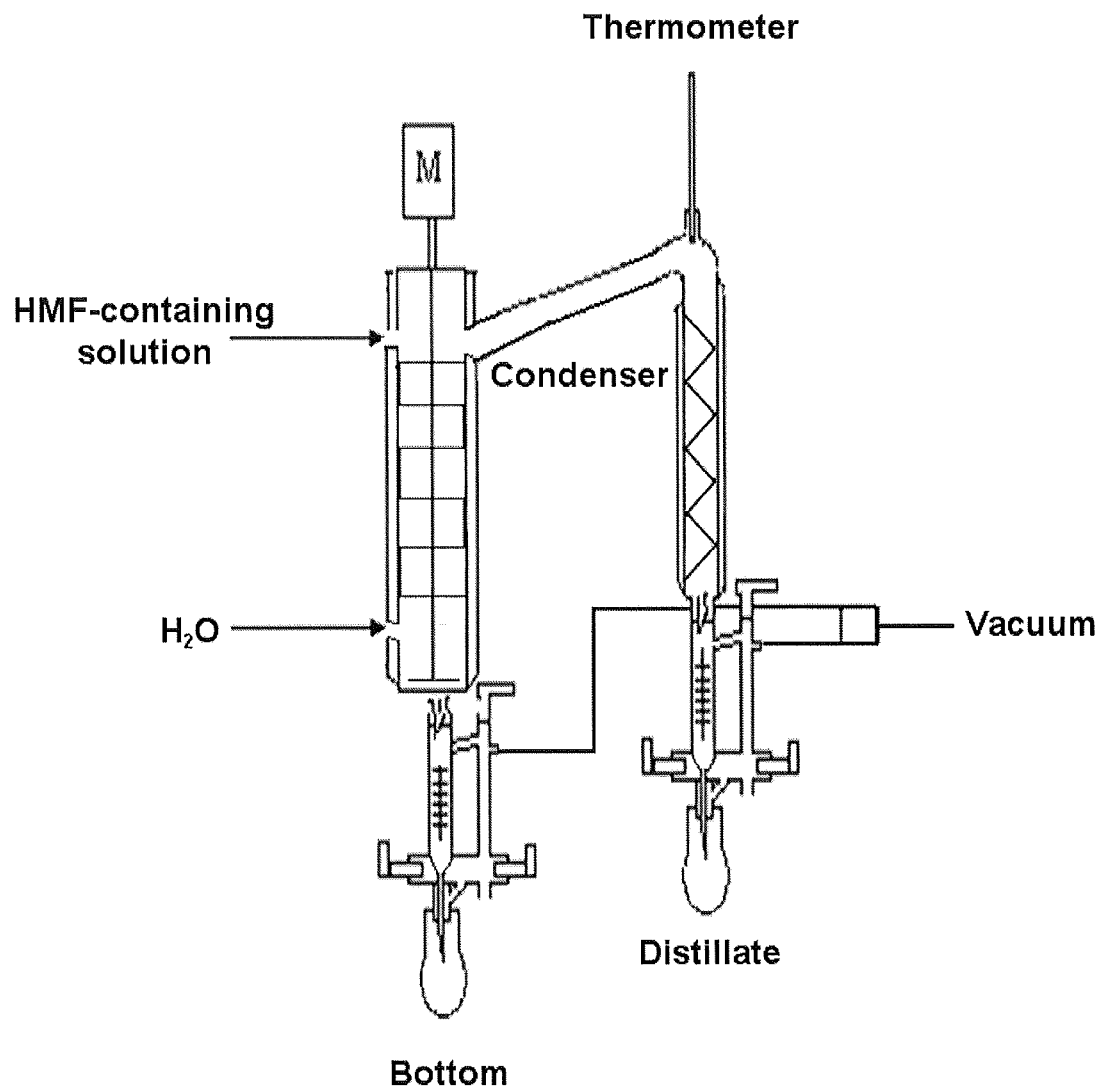

PRODUCTION OF 5 HYDROXYMETHYULFURFURAL (HMF) FROM HEXOSE SOLUTIONS IN THE PRESENCE OF STEAM

CROSS-REFERENCE TO RELATED APPLICATIONS

This application claims the benefit of U.S. Provisional Application No. 61/569,795, filed Dec. 13, 2011, which is incorporated herein by reference.

The present invention relates to a method for producing 5-hydroxymethylfurfural (HMF), wherein
- a) solutions (hereinbelow called starting solution) which comprise
  - a hexose and
  - an organic solvent with a boiling point greater than 200° C. (at standard pressure) (for short called high-boiling component),
  - and steam are fed to a reaction vessel,
- b) in the reaction vessel, a conversion of the hexose to HMF takes place in the presence of steam with the simultaneous distillative removal of the HMF and
- c) as distillate, an aqueous, HMF-comprising solution (hereinbelow called distillate) is obtained.

Compounds which are obtained from renewable raw materials and can be converted easily by chemical reactions to compounds which can be used industrially are increasingly of importance for chemical syntheses.

In this connection, 5-hydroxymethylfurfural (HMF) is known; this can be produced from hexoses by various methods. For example, 2,5-furandicarboxylic acid is readily obtainable from HMF and is suitable as dicarboxylic acids for producing polymers, such as polyesters or polyurethanes, and can replace other dicarboxylic acids from non-renewable raw materials in industrial applications.

HMF is generally produced by acid-catalyzed dehydration of hexoses such as glucose or fructose.

The reaction product obtained is acidic solutions which, besides the HMF, comprise unreacted starting materials and/or by-products. During the HMF synthesis, as a rule only a partial conversion of the starting materials takes place in order to avoid the formation of by-products. In general, the solutions obtained therefore comprise unreacted starting materials such as hexoses or oligomers or polymers composed of hexoses. In the case of higher conversions, the amount of by-products increases.

Separating off the HMF from the reaction solution which comprise starting materials or by-products of the HMF synthesis is complex and hinders the accessibility of HMF.

For example, Feroz Kabir Kazi et al. describe in Chem Eng. J. 169 (2011), pages 329-338 separating off the HMF from the acidic reaction solution by a complex extraction method using an organic solvent (butanol); a solution of HMF in butanol is obtained.

DE-A 3601281 discloses a chromatographic separation method in which firstly any organic solvents are removed and the aqueous HMF solution is separated using an ion exchange column. The HMF fraction obtained is crystallized.

A further method of separating off HMF from the reaction solution is the conversion of the HMF to another compound which is easier to separate off, optionally followed by a back-conversion to HMF after separation has taken place. For example, according to Mark Mascal and Edward B. Nikitin in 2008 Angew. Chemie vol. 47, pages 7924-7926, HMF is converted to the more stable 5-chloromethylfurfural and then converted again to HMF or derivatives thereof. Alternatively, according to EP-A 1834950, the ethers or, according to EP-A 1834951, the esters of HMF are produced which, after separation has taken place, are directly suitable for further syntheses.

Haru Kawamoto, Shinya Saito et al. describe in J. Wood Sci. (2007), 53, pages 127-133 the pyrolysis of cellulose with the formation of levoglucosenone, furfural and/or HMF under various conditions, including with the introduction of steam.

HMF should be present for further syntheses in the purest possible form. Of particular suitability for further syntheses are aqueous solution of HMF which does not comprise by-products or residual starting materials, or at best comprises them in very small amounts. Methods known hitherto for producing HMF or aqueous solutions thereof with adequate purity are extremely complex.

The object of the present invention was therefore a method with which HMF can be produced in as simple and effective a manner as possible, HMF is obtained at the same time in the purest form possible and HMF is therefore separated off directly as completely as possible from reacted starting materials or by-products of the synthesis.

Accordingly, the method defined at the start has been found.

In the method according to the invention, HMF is produced in the presence of steam and separated off directly from by-products and unreacted starting materials of the HMF synthesis.

Process Step a)

In process step a), solutions (hereinbelow called starting solution) which comprise
  a hexose and
  an organic solvent with a boiling point greater than 200° C. (at standard pressure) (in short called high-boiling component),
and steam are fed to a reaction vessel.

The hexose is preferably fructose, glucose or mixtures of fructose and glucose. It is particularly preferably fructose or mixtures of fructose with glucose.

The starting solution can also comprise by-products or starting materials from the production of the hexose. For example, hexoses can be obtained by degradation of polymers such as cellulose or starch. The starting solution can therefore also comprise residual amounts of such polymers or their oligomeric degradation products.

The starting solution preferably comprises 1 to 40% by weight of hexose, particularly preferably 5 to 30% by weight of hexose, based on the total weight of the starting solution.

Preferably, the starting solution comprises less than 10% by weight, in particular less than 5% by weight and particularly preferably less than 1% by weight, of by-products or starting materials from the production of hexoses. In particular, the starting solution is essentially free from by-products and starting materials from the production of hexoses.

Furthermore, the starting solution comprises an organic solvent with a boiling point greater than 200° C. (at standard pressure), in particular greater than 250° C. (hereinbelow called in short high-boiling component).

Suitable high-boiling components are hydrophilic solvents; they may be protic, hydrophilic organic solvents, e.g. alcohols, or aprotic hydrophilic solvents, e.g. ethers or ketones, such as dimethyl sulfoxide.

Within the context of this invention, preferred high-boiling components are polyethers. The polyethers preferably have a melting point of less than 60° C., in particular of less than 30° C. (at standard pressure, 1 bar); particularly preferred polyethers are liquid at 20° C. (standard pressure).

The polyethers comprise at least two ether groups. The polyethers preferably comprise at least 3, in particular at least 4, particularly preferably at least 6, ether groups. In general, they comprise not more than 40, in particular not more than 30, ether groups, particularly preferably not more than 20 ether groups.

In a particular embodiment, the polyethers comprise no heteroatoms apart from oxygen in the form of ether groups and optionally hydroxyl groups.

In particular, they are aliphatic polyethers, particularly preferred polyethers are polyalkylene glycols, in which case the terminal hydroxyl groups can be etherified with alkyl groups, in particular C1- to C4-alkyl groups.

The alkylene groups of the polyalkylene glycols may be e.g. C2- to C10-, in particular C2- to C4-alkylene groups, such as ethylene, propylene or butylene groups. The polyalkylene glycols can also comprise different alkylene groups, e.g. in the form of blocks.

Very particular preference is therefore given to poly-C2- to C4-alkylene glycols, in particular polyethylene glycol, the terminal hydroxyl groups of which can be optionally etherified with alkyl groups; the number of repeat alkylene ether groups corresponds to the above number of ether groups, in particular the number of repeat alkylene ether groups is 4 to 30, particularly preferably 6 to 20. The terminal hydroxyl groups of the polyalkylene glycols can be etherified with alkyl groups, in particular C1- to C4-alkyl groups.

The starting solution can comprise the aforementioned high-boiling component as the sole solvent. In this case, the hexose is dissolved in the high-boiling component.

In a preferred embodiment, the starting solution comprises at least one further solvent besides the high-boiling component. The further solvent may be in particular water or hydrophilic organic solvents with a boiling point of less than 200° C. (low-boiling component), in which the hexose used should preferably be soluble, or mixtures of water with low-boiling components.

The further solvent is particularly preferably water. The starting solution is therefore particularly preferably an aqueous solution.

In one particular embodiment, the starting solution comprises, as solvent, exclusively water and the high-boiling component.

The starting solution comprises the high-boiling component, in particular the polyether, preferably in amounts of from 5 to 90% by weight, in particular from 30 to 80% by weight, particularly preferably from 50 to 70% by weight, based on the total weight of the starting solution.

Preferably, the content of low-boiling components in the starting solution is less than 50% by weight, in particular less than 30% by weight and particularly preferably less than 20% by weight.

The starting solution furthermore preferably comprises an acid. Acids catalyze the conversion of hexose to HMF. Suitable acids are heterogeneous acids, which are dispersed in the starting solution, or homogeneous acids, which are dissolved in the starting solution.

The starting solution preferably comprises a homogeneous acid. Suitable homogeneous acids are any desired inorganic or organic acids. By way of example, mention may be made of para-toluenesulfonic acid, methanesulfonic acid ($MeOSO_3H$), oxalic acid, sulfuric acid, hydrochloric acid or phosphoric acid. The starting solution comprises the acid preferably in amounts of from 0.1 to 10 mol % (based on the hexose), particularly preferably from 0.1 to 5 mol %.

Preferred starting solutions comprise e.g.
1 to 40% by weight of hexose
5 to 90% by weight of high-boiling component, preferably polyether
1 to 50% by weight of water
0.1 to 10 mol % of acid (based on the hexose)
0 to 10% by weight of other constituents, e.g. by-products from the synthesis of the hexose,
based on the total weight of the solution.

Particularly preferred starting solution comprise e.g.
5 to 30% by weight of hexose
30 to 80% by weight of high-boiling component, preferably polyether
10 to 50% by weight of water
0.1 to 5 mol % of acid (based on the hexose)
0 to 5% by weight of other constituents, e.g. by-products from the synthesis of the hexose,
based on the total weight of the solution.

The starting solution described above and steam are fed to a reaction vessel.

Process Step b)

In process step b), the conversion of the starting solution to HMF takes place in conjunction with a steam distillation known per se. For this purpose, the starting solution is brought into contact with the steam in the reaction vessel.

The treatment of the starting solution with steam takes place preferably at reduced pressure, in particular a pressure of from 1 to 300 mbar is contemplated. In particular, the pressure in the reaction vessel is 1 to 100 mbar, particularly preferably 1 to 50 mbar and, in a very particularly preferred embodiment, 1 to 40 or 1 to 35 mbar.

The treatment of the starting solution with steam takes place preferably at a temperature of the starting solution of from 100 to 200° C., particularly preferably from 120 to 180° C. and particularly preferably from 140 to 180° C. and very particularly preferably 150 to 180° C.

Preferably, the method according to the invention is operated continuously.

To this end, the starting solution and the steam are fed to the reaction vessel continuously and the product obtained, or distillate, is drawn off continuously.

The volume streams depend on the size and separation efficiency of the selected reaction vessel.

In a preferred embodiment, the ratio of the supplied volume of steam to the volume of supplied starting solution is in a range from 0.5 to 2 volume units of steam per 1 volume unit of starting solution, particularly preferably in the range from 0.8 to 1.5 volume units of steam per 1 volume unit of starting solution and in particular 0.8 to 1.2 volume units of steam per 1 volume unit of starting solution.

Suitable reaction vessels are customary evaporators which are set up for the introduction of starting solution and steam and in particular for the continuous procedure described above.

Preferred evaporators are thin-film evaporators. In these, the starting solution is present in the evaporator as a liquid film.

Particular preference is given to vertical thin-film evaporators; vertical thin-film evaporators of this type are known under equipment names such as "Luwa" or in particular "Sambay".

The preferred vertical thin-film evaporators are ultimately a perpendicular tube with internal devices for distributing and mixing the starting solution and external devices for heating the tube wall.

The starting solution is preferably fed in in the upper part of the thin-film evaporator and distributed as film on the heated tube wall. Steam can be fed to the evaporator, preferably to the thin-film evaporator, together with the starting solution or at any other desired point of the evaporator. The starting solution and the steam can be passed to the evaporator in the same direction (cocurrent) or in the opposite direction (countercurrent).

Preferably, the steam is supplied countercurrently to the starting solution. For this purpose, the starting solution is fed in in particular in the upper part of the evaporator, and the steam is fed in in the lower part of the evaporator.

The steam and the volatile constituents of the starting solution are preferably discharged via a separator at the top of the evaporator and condensed (distillate).

The nonvolatile constituents pass through the evaporator and are separated off as a liquid bottom product.

FIG. 1 shows a corresponding apparatus consisting of thin-film evaporator (Sambay) and device for the condensation.

The reaction in process step b) can be carried out as desired such that only a partial conversion of the hexose to the HMF or a complete conversion of the hexose to HMF takes place. In the case of a partial conversion, unconverted hexose can be reacted again; a complete conversion can increasingly result in the formation of by-products, in particular so-called humines, i.e. oligomers of the HMF.

Preferably, at least 40% by weight, in particular at least 60% by weight and, in a particular embodiment, at least 80% by weight of the hexose are converted.

Process Step c)

As distillate, an aqueous, HMF-comprising solution is obtained. The distillate comprises the HMF formed during the conversion and water from the steam distillation.

The distillate comprises in particular more than 60%, in particular more than 80%, of the HMF obtained overall during the conversion.

Moreover, the distillate can also comprise high-boiling component. If polyether is used as high-boiling component, the distillate comprises no or only small amounts of high-boiling component; the content of polyether in the distillate is then in particular less than 5% by weight, preferably less than 2% by weight and particularly preferably less than 1 or less than 0.5% by weight, based on the total weight of the distillate.

By-products which are formed during the conversion of the hexose to HMF are in particular humins (oligomers of the HMF). During the method according to the invention, the humins are essentially not produced in the distillate, but in the bottom (see FIG. 1).

The distillate therefore comprises no or only very small amounts of humins; the content of humins in the distillate is generally less than 2, in particular less than 0.5 and particularly preferably less than 0.1% by weight. The distillate is clear and has a slight yellow coloration.

Furthermore, the distillate comprises no or only small amounts of unconverted hexose; unconverted hexose is found predominantly in the bottom.

The content of unconverted hexose in the distillate is generally less than 5% by weight, in particular less than 2% by weight and particularly preferably less than 1% by weight.

It is an advantage of the method according to the invention that by-products of the HMF synthesis, polyether as high-boiling component and unconverted hexose are essentially produced in the bottom.

HMF is obtained in the production method according to the invention directly as distillate with high purity. The method according to the invention is therefore a simple and effective method for producing HMF and simultaneously separating off HMF from by-products and unconverted starting materials.

The distillate is suitable for chemical syntheses in which HMF is used as starting material. In particular, the distillate is suitable for chemical syntheses in which the starting material HMF is desired or required in high purity. By way of example, mention be made here of the use of the product solution for producing 2,5-furandicarboxylic acid or 2,5-bis(hydroxymethyl)furan.

EXAMPLES

Example 1

In-Situ Dehydration of Fructose and Isolation of HMF by Means of Steam Distillation Starting Solution The starting solutions were obtained by mixing pure substances. The starting solutions comprised fructose, high-boiling component, acid and water (see table).

The high-boiling components used were:
DMSO: dimethyl sulfoxide
PEG-600: a polyethylene glycol with a molecular weight of 600
Tetraglyme: tetraethylene glycol dimethyl ether The acids used were:
$H_2SO_4$: sulfuric acid
p-TSA: para-toluenesulfonic acid
MSA: methanesulfonic acid
Oxalic acid Carrying Out the Steam Distillation The steam distillation is carried out in the apparatus as in FIG. 1. The apparatus consists of a glass Sambay, which is operated in countercurrent procedure.

The starting solution was fed in at the top, and the steam was fed in in the lower third.

The composition of the starting solution for various high-boiling components and also the selected temperatures and pressures are listed in the table.

The stated temperature is that of the heating medium at the external wall of the tube, which is a good approximation to that of the liquid film of the starting solution at the internal wall of the tube.

The experiments were carried out continuously; each new temperature and pressure adjustment was followed by a waiting period until a steady state was reached.

The composition was determined by means of HPLC.

The stated conversions of fructose arise from the residual amounts of fructose in the bottom and distillate; fructose was converted to HMF and to by-products (humins).

The stated catalytic amounts of acid are based on fructose. The yield of HMF is the percentage fraction of the HMF in the distillate or in the bottom, based on the fructose content in the starting solution.

| High-boiling component | Conc. of high-boiling component [% by wt.] | Conc. of fructose [% by wt.] | Acid | Amount of acid [mol %, based on mol of fructose] | Temperature [° C.] | Pressure [mbar] | Fructose [% by wt.] in the distillate | Fructose [% by wt.] in the bottom | HMF [% by wt.] in the distillate | HMF [% by wt.] in the bottom | Fructose conversion [%] | Yield of HMF [%] Distillate | Yield of HMF [%] Bottom |
|---|---|---|---|---|---|---|---|---|---|---|---|---|---|
| Tetraglyme | 50 | 10 | Oxalic acid | 18 | 160 | 180 | 0.01 | 0.00 | 0.44 | 0.0 | 99.7 | 18.6 | 0.0 |
| DMSO | 90 | 10 | $H_2SO_4$ | 0.9 | 160 | 180 | 0.00 | 0.00 | 0.90 | 0.00 | 100.0 | 17.21 | 0.0 |
| DMSO | 90 | 10 | $H_2SO_4$ | 0.01 | 110 | 380 | 0.00 | 5.43 | 0.05 | 2.94 | 72.1 | 1.0 | 21.6 |
| PEG-600 | 49 | 24 | MSA | 0.6 | 160 | 25 | 0.17 | 5.73 | 1.73 | 0.22 | 80.9 | 19.1 | 1.0 |
| PEG-600 | 49 | 24 | MSA | 1.0 | 160 | 30 | 0.16 | 0.13 | 1.87 | 0.26 | 98.5 | 19.9 | 1.0 |
| PEG-600 | 49 | 24 | p-TSA | 1.0 | 160 | 30 | 0.03 | 0.07 | 2.12 | 0.39 | 99.6 | 22.2 | 0 |
| PEG-600 | 49 | 24 | Oxalic acid | 1.0 | 160 | 30 | 0.17 | 12.72 | 0.40 | 0.31 | 65.7 | 4.0 | 1.2 |

The invention claimed is:

1. A method for producing 5-hydroxymethylfurfural (HMF), comprising
   a) feeding a starting solution which comprises
      a hexose and
      a high-boiling component which comprises an organic solvent with a boiling point greater than 200° C. (at standard pressure),
   to a reaction vessel,
   b) in the reaction vessel, converting the hexose to HMF in the presence of steam with the simultaneous distillative removal of the HMF and
   c) obtaining a distillate comprising an aqueous, HMF-comprising solution.

2. The method according to claim 1, wherein the hexose is fructose, glucose or mixtures of fructose and glucose.

3. The method according to claim 1, wherein the high-boiling component is a polyether.

4. The method according to claim 3, wherein the polyether is a poly-C2- to C4-alkylene glycol, the terminal hydroxyl groups of which are optionally etherified with C1-C4 alkyl groups.

5. The method according to claim 1, wherein the starting solution comprises the high-boiling component in amounts of from 5 to 90% by weight.

6. The method according to claim 1, wherein the starting solution is an aqueous solution.

7. The method according to claim 1, wherein the reaction to give HMF takes place in the presence of an acid which is soluble in the starting solution.

8. The method according to claim 1, wherein the reaction to give HMF takes place at 100° C. to 200° C.

9. The method according to claim 1, wherein the reaction to give HMF takes place at a pressure of from 1 to 300 mbar.

10. The method according to claim 1, wherein the method is carried out continuously, where the starting solution and steam are fed to the evaporator continuously and the product solution is drawn off continuously.

11. The method according to claim 1, wherein the reaction vessel is a thin-film evaporator.

12. The method according to claim 1, wherein the steam is fed countercurrently to the starting solution.

13. The method according to claim 1, wherein more than 60% of the HMF obtained are in the distillate.

14. A process comprising:
   a) producing HMF by the method according to claim 1; and
   b) producing 2,5-furandicarboxylic acid or 2,5-bis(hydroxymethyl)furan from the HMF.

15. The method according to claim 1, wherein the ratio of the volume of steam used in relationship to the volume of starting solution is from 0.5:1 to 2:1.

16. The method according to claim 1, wherein at least 40% of the hexose is converted to HMF in the method.

17. The method according to claim 1, further comprising:
   d) discharging the steam and the volatile constituents of the starting solution via a separator at the top of an evaporator; and
   e) condensing the steam and the volatile constituents to form the distillate.

* * * * *